United States Patent
Bandeen

(10) Patent No.: US 7,331,781 B1
(45) Date of Patent: Feb. 19, 2008

(54) ORTHODONTIC EXPANDER FOR INCREASING MAXILLARY TRANSVERSE DIMENSION AND METHOD

(76) Inventor: Roger L. Bandeen, 322 Gethings Cir., Battle Creek, MI (US) 49015

(*) Notice: Subject to any disclaimer, the term of this patent is extended or adjusted under 35 U.S.C. 154(b) by 125 days.

(21) Appl. No.: 11/116,980

(22) Filed: Apr. 28, 2005

(51) Int. Cl.
A61C 3/00 (2006.01)

(52) U.S. Cl. .......................................... 433/7

(58) Field of Classification Search ................... 433/7, 433/18; 606/71, 105
See application file for complete search history.

(56) References Cited

U.S. PATENT DOCUMENTS

| | | | |
|---|---|---|---|
| 3,800,420 A * | 4/1974 | Ouaknine | 433/7 |
| 3,832,778 A | 9/1974 | Wallshein | 32/14 E |
| 4,107,843 A | 8/1978 | Spino et al. | 32/14 E |
| 4,323,345 A * | 4/1982 | Wallshein | 433/7 |
| 4,571,178 A * | 2/1986 | Rosenberg | 433/18 |
| 5,281,133 A | 1/1994 | Farzin-Nia | 433/7 |
| 5,439,377 A | 8/1995 | Milanovich | 433/7 |
| 5,472,344 A | 12/1995 | Binder et al. | 433/7 |
| 5,564,920 A | 10/1996 | Klapper et al. | 433/7 |
| 5,775,898 A | 7/1998 | Schellino et al. | 433/7 |
| 5,885,290 A | 3/1999 | Guerrero et al. | 606/71 |
| 5,904,479 A | 5/1999 | Staples | 433/7 |
| 5,919,042 A | 7/1999 | Williams | 433/19 |
| 5,975,894 A * | 11/1999 | Pozzi | 433/7 |
| 6,036,488 A | 3/2000 | Williams | 433/19 |
| 6,171,313 B1 * | 1/2001 | Razdolsky et al. | 606/86 |
| 6,213,766 B1 | 4/2001 | Di Massa | 433/7 |
| 6,241,517 B1 | 6/2001 | Williams | 433/19 |
| 6,267,589 B1 | 7/2001 | Farzin-Nia et al. | 433/7 |
| 6,299,439 B1 | 10/2001 | Kooiman | 433/7 |
| 6,302,687 B1 | 10/2001 | King | 433/7 |
| 6,309,213 B1 | 10/2001 | Forster | 433/7 |
| 6,328,745 B1 | 12/2001 | Ascherman | 606/86 |
| 6,334,771 B1 | 1/2002 | Liou | 433/7 |
| 6,450,806 B2 | 9/2002 | Winsauer | 433/7 |

(Continued)

FOREIGN PATENT DOCUMENTS

EP 308645 A1 * 3/1989

OTHER PUBLICATIONS

International Search Report, PCT/US06/15868, May 11, 2007.
Written Opinion Of The International Searching Authority, PCT/US06/15868, May 11, 2007.

*Primary Examiner*—John J Wilson
(74) *Attorney, Agent, or Firm*—Baker, Donelson, Bearman, Caldwell & Berkowitz

(57) ABSTRACT

An orthodontic expander with opposing bodies interconnected by a shaft threaded on opposing ends in opposing directions so that rotation of the shaft by engagement of a rotation body with a tool moves the bodies together or apart on guide pins extending between the bodies, and a jam nut threadably received on the shaft and selectively movable against one of the bodies to fix the bodies in a selected spaced-apart relation, with connectors extending between the bodies and the palate to apply lateral force to the palate. At least one of the guide pins includes demarcations for tracking expansion progress during treatment. A slot in a guide bore for the guide pin defines an interior stop wall that contacts a fin extending from the one guide pin to prevent separation. A method of locking expander bodies from slippage is disclosed.

20 Claims, 2 Drawing Sheets

U.S. PATENT DOCUMENTS

| | | |
|---|---|---|
| 6,482,001 B2 | 11/2002 | Farzin-Nia et al. ............. 433/7 |
| 6,499,996 B2 | 12/2002 | Forster ........................... 433/7 |
| 6,520,772 B2 | 2/2003 | Williams ........................ 433/7 |
| 6,592,366 B2 | 7/2003 | Triaca et al. .................... 433/7 |
| 6,644,967 B2 | 11/2003 | Ceppatelli et al. .............. 433/7 |
| 6,783,361 B2 * | 8/2004 | Huge et al. ..................... 433/7 |
| 2002/0006596 A1 | 1/2002 | Wensauer ....................... 433/7 |
| 2002/0025502 A1 | 2/2002 | Williams ....................... 433/19 |
| 2002/0172909 A1 | 11/2002 | Williams ....................... 433/19 |
| 2003/0013061 A1 | 1/2003 | Lauren et al. .................. 433/3 |
| 2003/0049581 A1 | 3/2003 | DeLuke .......................... 433/7 |
| 2004/0009450 A1 | 1/2004 | Clark ........................... 433/18 |
| 2004/0013996 A1 | 1/2004 | Sapian ......................... 433/18 |

* cited by examiner

Fig. 2
Fig. 3
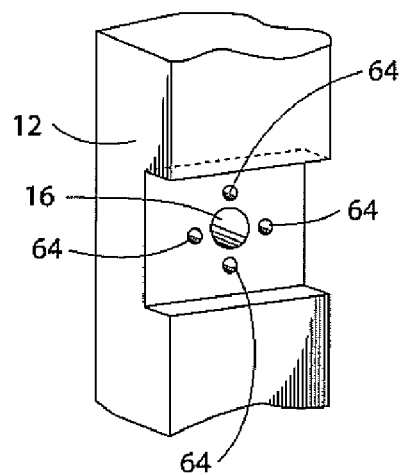
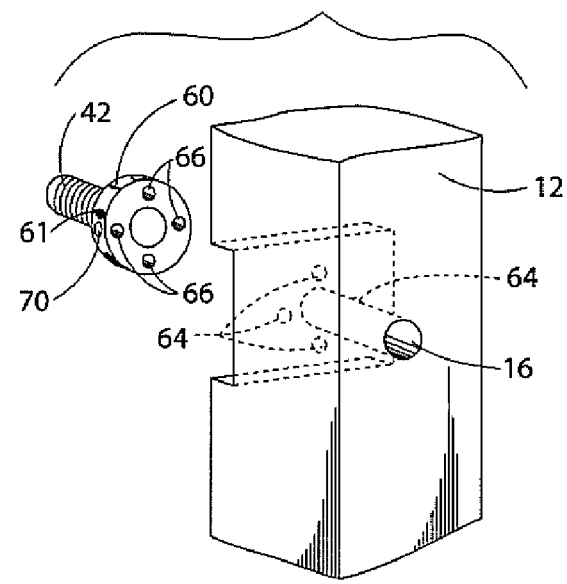
Fig. 4
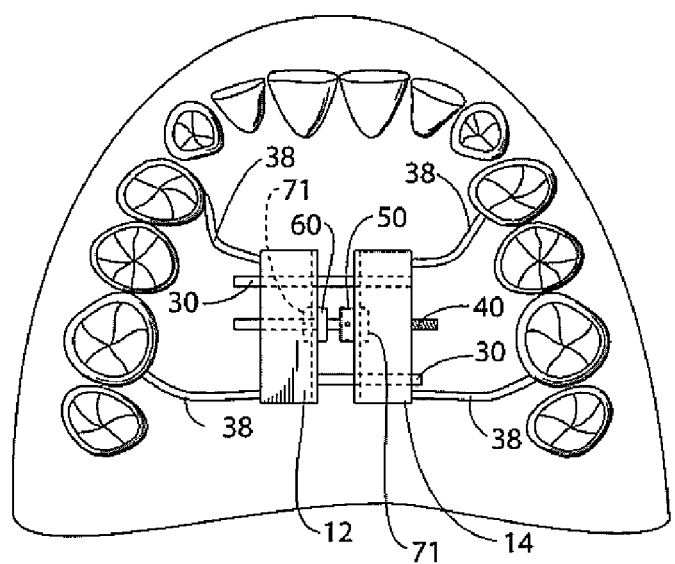

ORTHODONTIC EXPANDER FOR INCREASING MAXILLARY TRANSVERSE DIMENSION AND METHOD

TECHNICAL FIELD

The present invention relates to orthodontic expanders. More particularly, the present invention relates to apparatus and methods for improved operational features for orthodontic expanders for locking the orthodontic expander from slippage during treatment of increasing maxillary transverse dimension, for tracking expansion progress during treatment, and for providing directional and operational indicators that facilitate periodic adjustments during treatment.

BACKGROUND OF THE INVENTION

Orthodontic expansion is an occasionally required dental procedure to provide additional spacing for the teeth of a person. Particularly, orthodontic expanders function to expand the midpalatine suture of a patient and thereby increasing the maxillary transverse dimension in patients with maxillary transverse hypoplasia. Current known orthodontic expanders each include a screw that upon rotation causes opposing portions of the expander to move apart. Legs extending from the expander attach to orthodontic bands engaged to teeth. The legs communicate the laterally outward force from the expander to the maxillary suture of the patient. The continued application for laterally outward force causes the transverse dimension to increase slowly.

While orthodontic expanders have accomplished the goals of increasing the maxillary transverse dimension, there are drawbacks to their use. The available devices can experience slippage from frictional torque failure by which the screws turn back or slip from a setpoint. This leads to lost treatment time and additional clinical visits. The patient experiences frustration with the treatment and the orthodontic practice invests time and labor that could otherwise be directed to other patients. Also, present screw devices lack accurate indicators of the amount of opening being experienced during treatment, in part due to slippage, but also to inaccurate rotation count by the patient during interim adjustments of the expansion device, and inexact intraoral measurements.

Another potential problem is over-opening the expansion device that can result in separation of the end of the screw from the expansion device. Separation requires removal and reinstallation of the expansion device typically on an emergency or rush basis. Further, separation can require a re-start of the expansion process after stabilization. At the conclusion of the expansion process, the expansion device must be held in place for three months or more, in order for the stretched midpalatine suture (synchondrosis) to be stably replaced with bone structure.

Further, orthodontic expanders are custom fit to the upper palate of a patient with the legs soldered to the expander. Occasionally, unexpected position adjustments of the orthodontic expander are required. The particular orthodontic expander must be removed and discarded. Orthodontic expanders are also typically discarded upon completion of treatment.

Accordingly, there is a need in the art for orthodontic expanders that have any one (or more) of the improved operational features of locking in-place to resist slippage during treatment, providing directional and adjustment indicators that facilitate tracking of treatment with periodic adjustments, restricting apparatus separation, and facilitating economical treatment by not having to discard the expander after use. It is to such independent operating features that the present invention is directed.

BRIEF SUMMARY OF THE INVENTION

The present invention meets the needs in the art by providing an improved orthodontic expander that includes one or more features of locking in-place to resist slippage during treatment, providing directional and adjustment indicators to facilitate tracking of treatment with periodic adjustments, restricting apparatus separation, and providing economical treatment with reusable components that are not discarded after treatment use. In one aspect, the improved orthodontic expander comprises a pair of opposing bodies that each define a threaded bore, with an adjacent guide bore and a guide pin extending from the body. The threads of the threaded bores are turned in opposing directions and the guide pins extending from the respective body are received in the guide bore of the opposing body. A threaded member having a first portion threaded in a first direction and a second portion threaded in an opposing second direction threadably engage a respective threaded bore of the opposing bodies, whereby rotation of the threaded member moves the opposing bodies together or apart selectively. A rotation member is rigidly attached to the threaded member medial opposing distal ends and defines a plurality of openings in a perimeter surface of the rotation member for engaging by a tool to rotate the threaded member selectively in a first direction and in a second opposing direction. A jam nut threadably received on the first portion of the threaded member is selectively movable against the body receiving the first portion of the threaded member to fix the opposing bodies in a selected spaced-apart relation. Legs connect the opposing bodies to a respective tooth for applying lateral force to a palate.

In another aspect, the present invention provides a method of locking an orthodontic expander, comprising the steps of:

(a) positioning a pair of bodies in opposing relation for relative movement, each body defining a threaded bore, an adjacent guide bore, and a guide pin extending from the body, the threads of the threaded bores turned in opposing directions and the guide pins extending from the respective body for being received in the guide bore of the opposing body, the opposing bodies joined together for relative movement by a threaded member having a first portion threaded in a first direction and a second portion threaded in an opposing second direction that threadably engage a respective threaded bore of the opposing bodies, whereby rotation of the threaded member moves the opposing bodies together or apart selectively;

(b) moving a jam nut threadably received on the first portion of the threaded member to a distally spaced-apart position relative to the body that receives the first portion of the threaded member;

(c) rotating the threaded member to move the opposing bodies apart relative to each other; and (d) moving the jam nut against a side face of the body receiving the first portion of the threaded member, to lock the threaded member from rotation.

Features, objects, and advantages of the present invention will be apparent upon reading the following detailed description in conjunction with the claims and the appended drawings.

BRIEF DESCRIPTION OF THE DRAWINGS

FIG. 2 is a perspective detailed view of an expansion body used in the orthodontic expander illustrated in FIG. 1.

FIG. 3 is a perspective detailed view of a jam nut used with the orthodontic expander illustrated in FIG. 1.

FIG. 4 is a top plan view of the orthodontic expander mounted to teeth of a dental arch for expansion therewith.

DETAILED DESCRIPTION

Figure 1:
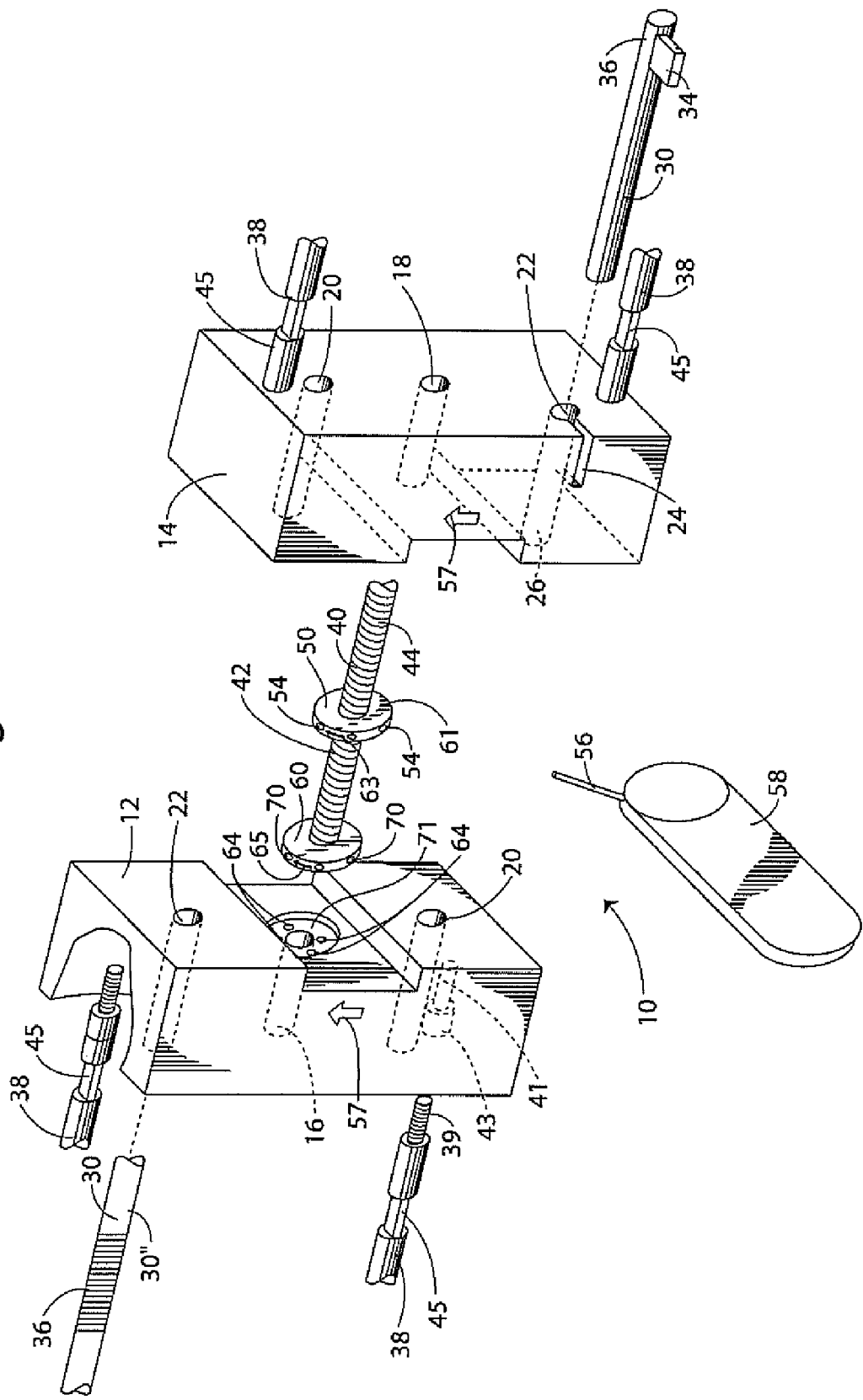
FIG. 1 is perspective exploded view of the orthodontic expander according to the present invention.

Referring now in more detail to the drawings, in which like numerals indicate like parts throughout the several views, FIG. 1 illustrates in perspective exploded view an orthodontic expander 10 according to the present invention. The orthodontic expander 10 comprises a pair of opposing bodies 12, 14 that each defines a respective threaded travel bore 16, 18 substantially central to the body. The threads of the travel bores 16, 18 are turned in opposing directions for a purpose discussed below. Each body includes a pair of guide bores 20, 22 spaced-apart from the travel bore 16, 18. One guide bore 22' defines a key slot 24 that extends from an outward face of the body 14 substantially to but short of the opposing face of the body. An inward face 26 of the body 14 defines a stop 26 in the key slot 24 as discussed below.

The guide bores 20, 22 receive a respective guide pin 30. One guide pin 30' includes a fin 34 that extends outwardly from an opposing end 36 parallel to a longitudinal axis of the guide pin. The fin 34 travels in the key slot 24 and a distal edge of the fin is visible from outside of the body 14 through an open face of the key slot 24. The guide pin 30' passes through the open key slot 24 of the body 14, the aligned opposing guide bore 20 in the body 12, and is secured at one end to the opposing body 12 (so that the opposing fin end is free to move relative to the body 14.)

The other guide pin 30" is fixed at one end to the housing 14 and an opposing distal end is free relative to the housing 12. The distal end portion includes dimensional interval markings 36 (such as millimeter intervals) visible on the portion that slidingly moves outwardly of the body 12 during movement of the bodies 12, 14 during treatment. The millimeter markings are observed relative to a flush position on an outward edge of the body 12. Upon opening of a gap between the bodies 12, 14 by turning a rotation number 50 (discussed below), the millimeter markings appear sequentially to indicate the amount of opening and thus the amount of increased maxillary transverse dimension.

Legs 38 extend from the bodies 12, 14 and connect to orthodontic bands attached to teeth, as best illustrated in FIG. 4. The legs 38 attach conventionally at one end with soldering to respective orthodontic bands. A bar connects between the legs 38 near the teeth to provide rigidity and equalize the force. An opposing end of the legs 38 define a threaded portion 39 that engages a threaded bore 41 in an outward face of the bodies 12, 14 as best illustrated in FIGS. 1 and 4. In the illustrated embodiment, the threaded bore 41 is countersunk with a non-threaded portion 43. In this way, bending of the leg 38 occurs remote from the threads of the leg to reduce shear at the threaded portion. The legs 38 define a flat 45 for engagement by a tool for tightening the leg during fabrication and removal of legs. The removable legs allow expander re-use. Further, should a leg break during appliance fabrication, the broken leg can be discarded and replaced without discarding the entire appliance.

With continuing reference to FIG. 1, as noted above, the guide pin 30" includes the series of uniformly spaced demarcations 36, such as one millimeter spacings. In one embodiment, the demarcations are spaced grooves, rings, or lines. In one embodiment in which the demarcations 36 are spaced lines, the dimensional length of the line provides an indication of the particular measuring unit, for example, a first length for 1 millimeter units, a second length greater than the first length for 5 millimeter units, and a third length greater than the second length for 10 millimeter units. In an alternate embodiment, the demarcations are alternating colors. The demarcations 36 facilitate counting and tracking expansion progress during treatment.

A shaft 40 extends between the bodies 12, 14. The shaft 40 is a threaded member having a first portion 42 threaded in a first direction and a second portion 44 threaded in an opposing second direction. The threaded portions threadably engage a respective threaded bore 16, 18 of the opposing bodies 12, 14, whereby rotation of the threaded shaft moves the opposing bodies 12, 14 together or apart selectively.

A rotation member 50 rigidly attaches to the threaded shaft 40 medial opposing distal ends. The rotation member 50 is disc-shaped or round with four equally spaced openings 54 (as illustrated, at 90° to one another) defined by two transverse through bores. A pin 56 extending from a tool 58 selectively inserts into one of the openings 54 for rotation of the threaded shaft 40 for adjusting the spacing of the bodies 12, 14. A directional indicator 57 for indicating the direction of rotation for moving the opposing bodies 12, 14 apart is central and medial to either the body 14 or 12.

A jam nut 60 threadably attaches to the first portion 42 of the threaded shaft 40. The jam nut 60 is selectively movable longitudinally on the threaded shaft to move into bearing contact with the face of the body 12. In this second position, the jam nut 60 fixes the opposing bodies 12, 14 in a selected spaced-apart relation. The inward face of the body 12 defines a plurality of spaced-apart shallow holes 64 (best illustrated in FIG. 2) arcuately spaced relative to the travel bore 16. The holes 64 receive one of a plurality of dimples 66 (best illustrated in FIG. 3) projecting from a side face of the jam nut 60. Engaging the dimples 66 in the holes 64 assists the fixing of the opposing bodies 12, 14 by the jam nut 60 in contact with the side of the body 12. The jam nut 60 similarly is disc-shaped or round with four openings 70 spaced equally apart (at 90° relative to each other) defined by two through bores. The pin 56 extending from the tool 58 selectively inserts into one of the openings 70 for rotation of the jam nut 60 during adjustment of the spacing of the bodies 12, 14.

The rotation member 50 can include a directional indicator 63 to indicate the direction of rotation for moving the opposing bodies 12, 14 apart. The jam nut 60 can include a directional indicator 65 to indicate the direction of rotation for releasing the jam nut from contact with the body 12 so that the rotation member 50 can be operated for moving the bodies apart.

In another aspect, the rotation member 50 and the jam nut 60 include distinguishing indicia generally 61. Not only are the two positionally differentiated, but each can include the distinguishing indicia 61 such as surface ornamentation, such as color, marking, symbol, or other distinguishing feature, to indicate the different function for the structural element. For example, the rotation member 50 in one embodiment is colored green and the jam nut 60 is colored red. This provides a visual indicator to the patient as to the adjustment activities during treatment as discussed below.

FIG. 1 further illustrates a recess feature 71 of an alternate embodiment of the bodies 12, 14. The inward faces of the bodies 12, 14 define the recess 71. The recesses 71 in the opposing bodies permit the bodies to move closely together during initial installation by providing respective recesses for receiving the rotation member 50 and jam nut 60.

With reference to FIGS. 1 and 4, the orthodontic expander 10 is gainfully used with the features of the present invention to facilitate maxmillary transverse expansion. The jam nut 60 is threaded on the first portion 42 of the shaft 40 which is positioned in alignment with the threaded travel bore 16. The guide pins 30' and 30" insert through the respective aligned guide bores 20, 22. One end of the guide pin 30' and 30" weld to a respective opposing body 12, 14. The bodies 12, 14 are brought together, with the fin 34 of the guide pin 30' in the slot 24. The shaft 40 is rotated to draw the bodies 12, 14 together moving on the guide pins 30 in the guide bores 20, 22. The orthodontic expander 10 is installed in a patient with the legs 38 extending to and connecting with orthodontic bands attached to teeth on opposing sides. The threaded legs 38 facilitate reinstallation of the orthodontic expander 10 as is necessary with some patients during treatment and also make the expander re-usable.

After attaching the orthodontic expander 10 to the teeth through connecting the legs 38 to the orthodontic bands, and periodically during treatment, the orthodontic expander is adjusted to apply lateral outward force on the teeth through the legs. This is accomplished by inserting the pin 56 into one of the holes 54 in the perimeter of the rotation member 50. The tool 58 is moved in order to rotate the threaded shaft 40. The directional indicator 57 and 63, such as a guide arrow, provides a visual sign that helps the patient rotate the shaft 40 in the direction to move the bodies 12, 14 apart. Rotation of the shaft 40 causes the bodies 12, 14 to move on the threaded portions 42, 44. Rotation in a first direction causes the bodies 12, 14 to move apart laterally, and thereby increase the force applied to the maxillary structure. The demarcations 36 on the guide pin 30 facilitate tracking of the progress of the treatment, by physical contact with the grooves or by visual observation of the grooves or the different coloring of the bands.

Upon positioning of the bodies 12, 14 in increased spaced relationship, the jam nut 60 is rotated on the threaded shaft to move the side of the jam nut into engagement with the body 12. The tool 58 is used with the pin 56 to rotate the jam nut 60. The dimples 66 snap into the respective holes 64 when the side of the jam nut contacts the body 12. The engagement of the dimples and the holes facilitate locking jam nut to the body and thus locking the bodes from inward slippage.

During periodic adjustment, the bodies 12, 14 move relatively apart as guided by the guide pins 30. The demarcations 36 can be observed to track treatment progress, such as moving a pick physically across the guide pin to count the demarcations or observing the demarcations.

As adjustments are made, the fin 34 on the guide pin 30 approaches and then is blocked by the inner face 26 or stop wall of the slot 24. The fin 34 in contact with the inner face 26 prevents further expansion of the bodies 12, 14, and thus prevents separation of the bodies. Maximum expansion is visually realized when the fin 34 contacts the end 26 of the open slot 24.

It is to be appreciated that the orthodontic expander of the present invention can be gainfully used with any one of the improved features disclosed herein chosen from locking in place to resist slippage during treatment, providing directional and adjustment indicators that facilitate tracking of treatment with periodic adjustments, restricting separation, and appliance re-use.

The present invention accordingly provides an orthodontic expander with features that individually address problems with orthodontic expansion treatments by proving an expander that resist slippage, that provides directional indicators for making periodic adjustments, that facilitates tracking of the treatment process, and that enables reuse of expander components. The principles, preferred embodiments, and modes of operation of the present invention have been described in the foregoing specification. The invention is not to be construed as limited to the particular forms disclosed because these are regarded as illustrative rather than restrictive. Moreover, variations and changes may be made by those skilled in the art without departure from the spirit of the invention as described by the following claims.

What is claimed is:

1. An orthodontic expander for increasing maxillary transverse dimension, comprising:
    a first body and an opposing second body that each define a threaded bore, a pair of guide bores, and a guide pin fixed to and extends from one of the guide bores in the body, the threads of the threaded bores turn in opposing directions, and the guide pins extending from the respective body for being slidably received in the aligned one of the guide bores of the opposing body;
    a threaded member having a first portion threaded in a first direction for engaging the threaded bore of the first body and a second portion threaded in an opposing second direction for engaging the threaded bore of the opposing second body, whereby rotation of the threaded member moves the opposing first and second bodies together or apart selectively;
    a rotation member rigidly attached to the threaded member medial opposing distal ends and defining a plurality of openings in a perimeter surface of the rotation member for engaging by a tool to rotate the threaded member selectively in a first direction and in a second opposing direction;
    a jam nut defining on a side face a plurality of laterally projecting lugs and threadably received on the first portion of the threaded member and selectively movable against the first body to fix the opposing bodies in a selected spaced-apart relation;
    the first body having an engaging surface that defines a plurality of detents spaced apart about the opening for receiving the lugs when the jam nut is threaded against the body, the receipt of the lugs within the detents restricting threaded member from rotation; and
    means for connecting the opposing bodies to a respective tooth for applying lateral force to a palate.

2. The orthodontic expander as recited in claim 1, further comprising a directional indicator fixed to one of the bodies for indicating the direction of rotation for moving the opposing bodies apart.

3. The orthodontic expander as recited in claim 1, wherein the rotation member includes a first identifying indica and the jam nut includes a second identifying indicia differing from the first identifying indicia.

4. The orthodontic expander as recited in claim 3, wherein the first and second identifying indicia are colors.

5. The orthodontic expander as recited in claim 1, wherein one of the bodies defines an open slot to the guide bore, the slot extending through the body a substantially entire distance from a surface that faces away from the opposing body to define a stop within the body; and wherein one guide pin includes a fin extending laterally from a distal end portion for relative travel through the slot until moved into contact with the stop by rotation of the threaded member while moving the bodies apart.

6. The orthodontic expander as recited in claim 1, wherein means for connecting comprises:
orthodontic bands attachable to teeth on opposing sides of the palate;
a pair of threaded bores on laterally outward faces of the bodies; and
legs that each have a threaded end for threadably engaging a respective one of the threaded bores and an opposing end for securing to a respective one of the orthodontic bands.

7. The orthodontic expander as recited in claim 6, wherein the threaded bore on the laterally outward face is countersunk to provide a non-threaded portion and a relatively recessed threaded portion.

8. The orthodontic expander as recited in claim 1, wherein the guide pin includes a plurality of spaced-apart dimensional indicies for monitoring movement of the opposing bodies during an orthodontic expansion treatment.

9. The orthodontic expander as recited in claim 8, wherein the dimensional indicies are grooves defined in the guide pin.

10. The orthodontic expander as recited in claim 8, wherein the dimensional indicies are differentiating colors applied to the guide pin.

11. The orthodontic expander as recited in claim 1, wherein an inward face of each of the bodies defines a recess for receiving the jam nut and the rotation member in a respective recess to facilitate the bodies closely spaced during initial installation of the orthodontic expander.

12. An orthodontic expander for increasing maxillary transverse dimension, comprising:
a pair of opposing bodies that each define a threaded bore and-at least one guide bore, and a guide pin fixed to and extending outwardly from the guide bore of one of the pair of bodies, the threads of the threaded bores turn in opposing directions and the guide pin extending from the respective body for being slidably received in the guide bore of the opposing body;
the guide pin includes a plurality of spaced-apart dimensional indicies for monitoring movement of the opposing bodies during an orthodontic expansion treatment;
a threaded member having a first portion threaded in a first direction and a second portion threaded in an opposing second direction for threadably engaging a respective threaded bore of the opposing bodies, whereby rotation of the threaded member moves the opposing bodies together or apart selectively;
a rotation member rigidly attached to the threaded member medial opposing distal ends and defining a plurality of openings in a perimeter surface of the rotation member for engaging by a tool to rotate the threaded member selectively in a first direction and in a second opposing direction;
a jam nut defining on a side face a plurality of laterally projecting lugs and threadably received on the first portion of the threaded member and selectively movable against the respective body to fix the opposing bodies in a selected spaced-apart relation;
the respective body having an engaging surface that defines a plurality of detents spaced apart about the opening for receiving the lugs when the jam nut is threaded thereagainst, the receipt of the lugs within the detents restricting threaded member from rotation; and
means for connecting the opposing bodies to a respective tooth for applying lateral force to a palate.

13. The orthodontic expander as recited in claim 12, wherein the dimensional indicies are grooves defined in the guide pin.

14. The orthodontic expander as recited in claim 12, wherein the dimensional indicies are differentiating colors applied to the guide pin.

15. The orthodontic expander as recited in claim 12, wherein an inward face of each of the bodies defines a recess for receiving the jam nut and the rotation member in a respective recess to facilitate the bodies closely spaced during initial installation of the orthodontic expander.

16. An orthodontic expander for increasing maxillary transverse dimension, comprising:
a pair of opposing bodies that each define a threaded bore, a pair of guide bore, and a guide pin fixed to and extending from one of the guide bores, the threads of the threaded bores turn in opposing directions, and each of the guide pins extending from the respective body for being slidably received in an aligned guide bore of the opposing body;
a threaded member having a first portion threaded in a first direction and a second portion threaded in an opposing second direction for threadably engaging a respective threaded bore of the opposing bodies, whereby rotation of the threaded member moves the opposing bodies together or apart selectively;
a rotation member rigidly attached to the threaded member medial opposing distal ends and defining a plurality of openings in a perimeter surface of the rotation member for engaging by a tool to rotate the threaded member selectively in a first direction and in a second opposing direction;
one of the bodies further defines a slot open to the guide bore, the slot extending through the body a substantially entire distance from a surface that faces away from the opposing body to define a stop within the body;
at least one of the guide pins having a fin that extends laterally from a distal end portion for relative travel through the slot until moved into contact with the stop during rotation of the threaded member to move the bodies apart;
a jam nut defining on a side face a plurality of laterally projecting lugs and threadably received on the first portion of the threaded member and selectively movable against the respective body to fix the opposing bodies in a selected spaced-apart relation;
the respective body having an engaging surface that defines a plurality of detents spaced apart about the opening for receiving the lugs when the jam nut is threaded thereagainst, the receipt of the lugs within the detents restricting threaded member from rotation; and
means for connecting the opposing bodies to a respective tooth for applying lateral force to a palate.

17. The orthodontic expander as recited in claim 16, wherein an inward face of each of the bodies defines a recess for receiving the jam nut and the rotation member in a respective recess to facilitate the bodies closely spaced during initial installation of the orthodontic expander.

18. An orthodontic expander for increasing maxillary transverse dimension, comprising:
a pair of opposing bodies that each define a threaded bore, a pair of guide bores, and a guide pin extending from one of the guide bores, the threads of the threaded bores turn in opposing directions, and the guide pins extending from the respective body for being received in the aligned guide bore of the opposing body;

a threaded member having a first portion threaded in a first direction and a second portion threaded in an opposing second direction for threadably engaging a respective threaded bore of the opposing bodies, whereby rotation of the threaded member moves the opposing bodies together or apart selectively;

a rotation member rigidly attached to the threaded member medial opposing distal ends and defining a plurality of openings in a perimeter surface of the rotation member for engaging by a tool to rotate the threaded member selectively in a first direction and in a second opposing direction;

orthodontic bands each attachable to a respective one of the teeth on opposing sides of the palate;

a pair of threaded bores on laterally outward faces of the bodies;

a plurality of legs each having a threaded end for threadably engaging a respective one of the threaded bores on the laterally outward faces and an opposing end for attaching to a respective one of the orthodontic bands;

a jam nut defining on a side face a plurality of laterally projecting lugs and threadably received on the first portion of the threaded member and selectively movable against the respective body to fix the opposing bodies in a selected spaced-apart relation; and the respective body having an engaging surface that defines a plurality of detents spaced apart about the opening for receiving the lugs when the jam nut is threaded thereagainst, the receipt of the lugs within the detents restricting threaded member from rotation.

19. The orthodontic expander as recited in claim 18, wherein an inward face of each of the bodies defines a recess for receiving the jam nut and the rotation member in a respective recess to facilitate the bodies closely spaced during initial installation of the orthodontic expander.

20. A method of locking an orthodontic expander during and after increasing maxillary transverse dimension, comprising the steps of:

(a) positioning a pair of bodies in opposing relation for relative movement, each body defining a threaded bore, an adjacent guide bore, and a guide pin extending from the body, the threads of the threaded bores turned in opposing directions and the guide pins extending from the respective body for being received in the guide bore of the opposing body, the opposing bodies joined together for relative movement by a threaded member having a first portion threaded in a first direction and a second portion threaded in an opposing second direction that threadably engage a respective threaded bore of the opposing bodies, whereby rotation of the threaded member moves the opposing bodies together or apart selectively;

(b) moving a jam nut threadably received on the first portion of the threaded member to a distally spaced-apart position relative to the body that receives the first portion of the threaded member, a side face of the jam nut defining a plurality of laterally projecting lugs;

(c) rotating the threaded member to move the opposing bodies apart relative to each other; and (d) moving the jam nut against a side face of the body receiving the first portion of the threaded member, said side face defining a plurality of detents spaced apart about the opening, to engage the lugs in the detents to lock the threaded member from rotation and thereby preventing the opposing bodies from slipping back towards each other.

* * * * *